United States Patent [19]
Knowlton

[11] Patent Number: 5,861,950
[45] Date of Patent: Jan. 19, 1999

[54] PARTICLE DETECTION SYSTEM UTILIZING AN INVISCID FLOW-PRODUCING NOZZLE

[75] Inventor: Dennis J. Knowlton, Boulder, Colo.

[73] Assignee: Particle Measuring Systems, Inc., Boulder, Colo.

[21] Appl. No.: 891,361

[22] Filed: Jul. 10, 1997

[51] Int. Cl.$^6$ .................................................. G01N 21/00
[52] U.S. Cl. ......................................................... 356/338
[58] Field of Search .................................. 356/336, 338, 356/339, 436

[56] References Cited

U.S. PATENT DOCUMENTS

| | | | |
|---|---|---|---|
| 4,178,103 | 12/1979 | Wallace | 356/336 |
| 4,737,025 | 4/1988 | Steen | 356/39 |
| 5,067,814 | 11/1991 | Suzuki et al. | 356/339 |
| 5,282,151 | 1/1994 | Knollenberg | 364/555 |
| 5,481,357 | 1/1996 | Ahsan et al. | 350/338 |
| 5,515,164 | 5/1996 | Kreikebaum et al. | 356/339 |

Primary Examiner—Richard A. Rosenberger
Attorney, Agent, or Firm—Duft, Graziano & Forest, P.C.

[57] ABSTRACT

A particle detection system in which a beam of light is incident upon an inviscid jet of fluid. A sample fluid containing particles is passed through an inviscid flow producing nozzle. An inviscid flow jet is output from the nozzle. The entire inviscid flow jet moves with uniform velocity and can therefore be contained within the sample region for the detection system. A volumetric measurement is thereby achieved where all of the sample fluid moves with uniform velocity. Sample fluid is decelerated in a deceleration chamber to a velocity significantly less than the nozzle velocity. The nozzle has a length and a width where the ratio of length to width is less than about 1. Sample fluid flows from the deceleration chamber through the nozzle and is output from the nozzle in an inviscid flow jet into a collection chamber. An optical collector system collects light scattered by particles in the inviscid flow jet and images the scattered light on a detector. The shape of the inviscid flow jet can be circular or non circular. An inviscid flow jet having a high aspect ratio can be fully illuminated by a relatively focussed beam of light providing a highly sensitive measurement.

37 Claims, 5 Drawing Sheets

PARTICLE DETECTION SYSTEM UTILIZING AN INVISCID FLOW-PRODUCING NOZZLE

FIELD OF THE INVENTION

This invention relates to submicron-sized particle detection, and more particularly, relates to a device and method for particle detection utilizing a nozzle that produces an inviscid flow of the fluid in which the particles are detected.

STATEMENT OF THE PROBLEM

When a beam of radiant energy is incident upon a particle, a portion of the energy is scattered. The intensity of the scattered energy depends upon the wavelength of the incident radiant energy, upon the difference in refractive index of the particle with respect to the medium in which it is suspended, upon the size and shape of the particle, and upon the angle at the which the scattered energy is observed.

The measurement of fine, submicron-sized particles in fluids has developed significantly in recent years. In general terms, an approach exists for making such measurements whereby a beam of light is made incident upon a fluid carrying the particles to be measured. The particles in the fluid cause scattering of the incident light. The scattered light is collected and detected to produce a measure of the size and number of particles in the fluid. Examples of this particle detection approach are found in U.S. Pat. No. 4,798,465 issued to Knollenberg on Apr. 14, 1986 and assigned on its face to Particle Measuring Systems, Inc., U.S. Pat. No. 5,282,151 issued to Knollenberg on Jan. 25, 1994 and assigned on its face to Particle Measuring Systems, Inc. and U.S. Pat. No. 5,459,569 issued to Knollenberg et. al. on Oct. 17, 1995 and assigned on its face to Particle Measuring Systems, Inc.

A focus of much attention in this field has been the improvement of the sensitivity of instruments for making such measurements. The sensitivity of particle measuring instruments is defined by the smallest particle that can be detected. Generally, improvements in sensitivity have been achieved by using a more tightly focussed light beam. Because particle detection instruments are often used to detect particles in highly purified fluids, there are actually very few particles in the fluid in relation to the total volume of the fluid. To achieve a statistically significant measurement one must pass a relatively large volume of fluid through the measuring device. Therefore, the time to statistical significance for a particle detection measurement is directly related to the "sample volume" of the fluid within which the particles are carried. The sample volume is the volume within the intersection between the fluid flow and the incident light from which scattered light is collected onto the light detection system. As the incident light beam is focussed more narrowly to increase measurement sensitivity, the sample volume necessarily decreases. Therefore the time to statistical significance for a particle measurement generally speaking, increases with improvements in sensitivity for existing particle measurement instruments. An increase in the time to statistical significance is a problem because users of these instruments desire real-time information about their process and long measurement times can result in costly delays for needed process adjustments. Improvements in sensitivity also have come at the expense of measurement resolution. The resolution of a measurement device defines its ability to resolve differences in size between particles.

The maximum attainable sample volume is a sample volume through which all of the measured fluid passes. When all or nearly all of the measured fluid passes through the sample volume the measurement is referred to as being "volumetric". When less than about 90% of the measured fluid passes through the sample volume then the measurement is referred to as being "in-situ". A problem with larger-sized sample volumes in existing particle detection instruments is that the measured fluid moves with a non-uniform velocity in a profile substantially orthogonal to the direction of flow. Therefore the sample volume includes particles moving at different velocities. Particle detection schemes relying on scattered light are most effective and accurate, however, when each detected light-scattering particle moves at the same velocity. Existing particle detection instruments therefore either limit the sample volume to include only a portion of the fluid flow profile that is moving with substantially uniform velocity or only collect scattered light from the portion of the fluid flow profile that is moving with substantially uniform velocity.

U.S. Pat. No. 5,067,814 issued to Suzuki et al. on Nov. 26, 1991 and assigned on its face to Horiba Ltd. discloses an apparatus for measuring fine particles in fluids. The Horiba device includes a cell within which fluid is spurted in a stream from a nozzle. A laser emits a beam of light that is orthogonal to and incident upon the stream of fluid. A light detection system is arranged coaxially with the fluid stream and collects light scattered along the axis the of the fluid flow by particles in the fluid. Only light scattered from near the center of the stream of fluid has a relatively uniform velocity. Thus, the light detection system includes a variable stop that limits the scattered light reaching the detector to the light scattered from particles having relatively uniform velocity.

U.S. Pat. No. 4,178,103 issued to Wallace on Dec. 11, 1979 and assigned on its face to Chromatix, Inc. discloses a light scattering particle detection system employing an unsupported "curtain" of fluid. The Wallace device detects light orthogonally to the fluid flow and uses a means for forming a curtain of fluid upon which the light beam is incident. The purpose of the fluid curtain is to reduce scatter from the surface of the curtain as compared to a cylindrical jet or stream of water. The curtain has a central portion which is substantially flat and planar upon which the light beam is incident.

U.S. Pat. No. 5,282,151 issued to Knollenberg on Jan. 25, 1994 and assigned on its face to Particle Measuring Systems, Inc., discloses a noncircular fluid jet illuminated by a light source for detecting particles. No teaching is provided related to the uniformity of the fluid velocity across the fluid jet.

There exists a need for a particle detection system for detecting particles in a fluid where substantially all the fluid passes through the sample volume and all the fluid moves at substantially the same velocity.

STATEMENT OF THE SOLUTION

The above identified problems, and others, are solved and a technical advance is achieved in the field by the particle detection system of the present invention. The present invention produces an inviscid flow jet upon which is incident a beam of focussed light. Inviscid flow is fluid flow in which the fluid has a uniform velocity profile. Inviscid flow is sometimes referred to as "plug" flow. Since all of the fluid in the jet moves with substantially the same velocity, all of the particles carried in the fluid move with substantially the same velocity. The apparatus of the present invention is formed to create a sample volume that includes substantially all of the fluid jet. Therefore a volumetric particle detection measurement is accomplished where all of the particles are moving at substantially the same velocity.

A viscous fluid experiences viscous drag as it interacts with the walls of the conduit within which it flows. An inviscid fluid is one that has no viscosity effects. Process fluids, such as used in the semiconductor fabrication industry, rarely if ever are inviscid. However, the particle detection system of the present invention employs a flow nozzle that creates an inviscid flow for purposes of a particle detection measurement.

Fluid is caused to flow under a nominal pressure of about 1–5 psi. The fluid is decelerated to a velocity significantly less than the jet velocity and is then exposed to the nozzle. The nozzle is formed so that the jet of fluid exiting the nozzle into a collection chamber has a uniform velocity across the jet. This is sometimes referred to as "laminar, inviscid flow" or "inviscid flow" or "plug flow" and is hereinafter referred to as inviscid flow. The entire inviscid flow jet is illuminated with a high intensity light source such as a laser. Particles in the jet traversing the illuminated section scatter light according to Mie or Rayleigh scattering theory. The scattered light is imaged, using an optical system, upon a detector for subsequent processing. Light scattered from all the particles can be collected since all of the particles in the inviscid flow jet travel at the same velocity. Both the concentration of particulate contamination and the size distribution of the particulate contamination is determined.

The nozzle has an aperture diameter and a thickness. An inviscid flow jet is produced from the nozzle when the ratio of the diameter to the thickness is about equal to or greater than 1. Each embodiment of the system of the present invention uses a nozzle meeting this characteristic measurement.

The uniformity of the jet is further enhanced by minimizing any boundary layer separation, i.e., turbulent eddies, occurring at the nozzle. This is accomplished by rounding the corners or edges of the inlet side of the nozzle aperture.

The inviscid flow jet need not be circular in cross-section. In one embodiment of the present invention, a nozzle having a high aspect ratio produces an inviscid flow jet. The highly elongated, oval-shaped jet is totally illuminated by the incident light just as in the circular jet embodiment. In addition, the laser is incident on the narrow dimension of the oval-shaped jet and is therefore focussed more narrowly. Thus, a high sensitivity, volumetric measurement is achieved.

In one embodiment of the present invention a sheath flow is utilized so that there is no relative velocity between the interface of the sample flow in the jet and the fluid in the collection chamber. Hydrodynamic focussing is used to merge a sample flow and a sheath flow so that the inviscid flow jet comprises a sample jet encased within the sheath jet. Thus there is no relative velocity between the sample jet and the sheath jet. This provides signal processing advantages as the sample jet is made even more uniform. Use of a sheath flow also helps improve the stability of a laser cavity where the present invention is applied in conjunction with a laser cavity.

The advantages of measuring scattered light from particles moving in an inviscid flow jet are obtained regardless of the axis on which the scattered light is detected. Scattered light can be detected on an axis orthogonal to the fluid flow axis, for example. Light scattered coaxially to the fluid flow can also be collected and detected. In one embodiment of the present invention, the detection system is coaxial to the fluid flow thus light scattered coaxial to the fluid flow is detected. One advantage of imaging on or nearly on-axis with the flow is that noise in the signal caused by molecular scatter can be reduced by imaging only on the intersection of the jet and the illumination, thereby not including the molecular scatter noise outside of the region of interest. Although on-axis detection is preferable, it is not required.

In an embodiment of the present invention, a sample fluid stream is merged with a sheath fluid stream in a decelerating chamber. At the lower end of the decelerating chamber is a nozzle from which is emitted an inviscid jet of fluid into a collection chamber. The nozzle is shaped to form a high aspect ratio, inviscid flow jet comprised of a sample flow encased within a sheath flow. The jet is essentially a flat sheet or curtain of fluid having a generally uniform velocity profile across the jet. Incident on the jet is an intense beam of light that is somewhat wider than the thickness of the jet and about 20 microns in height. The beam of light is aligned to travel through the longer dimension of the high aspect ratio jet. The detection system is arranged to collect light scattered coaxial to the fluid flow. All of the sample fluid and entrained particles are moving with substantially the same velocity. All of the sample fluid is illuminated by the light. The light can be tightly focussed, for high sensitivity, due to the elongated shape of the jet. The optical collection system collects light scattered from all of the particles in the sample fluid and images the scattered light onto the detector. High resolution and short measurement time are achieved since the measurement is volumetric. High sensitivity is achieved since the laser beam is focussed to provide high power in a relatively narrow line across the curtain-shaped jet.

The system of the present invention provides unmatched sensitivity and resolution characteristics for sub-micron sized particle detection.

Figure 1:
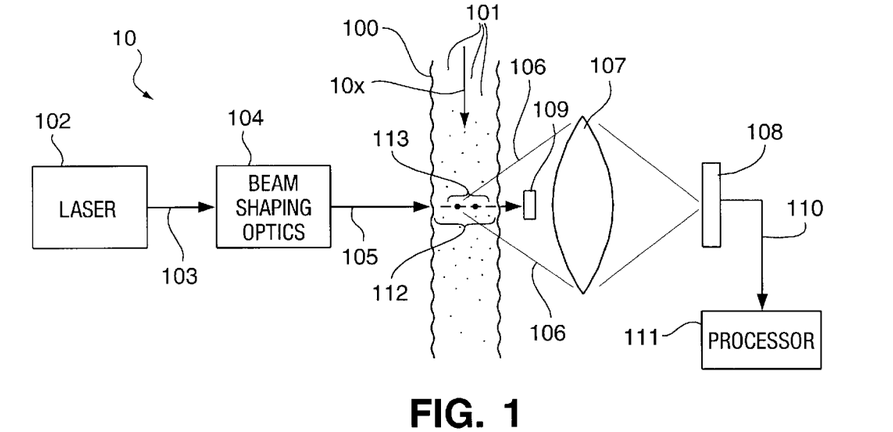
FIG. 1 is a schematic diagram of a generalized particle detection system.
Figure 2:
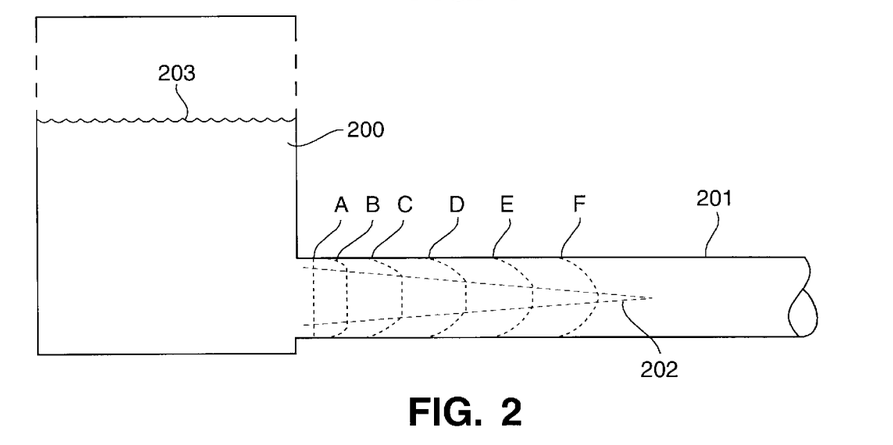
FIG. 2 depicts a conduit into which fluid flows from a tank.

DETAILED DESCRIPTION
Particle Detection Systems in General—FIGS. 1–2

Throughout the Detailed Description, multiple FIGS. having elements in common designate those common elements using the same reference numerals. FIG. 1 depicts a simplified schematic for a generalized particle detection system 10. FIGS. 1–2 depict known particle detection systems and principles and are presented here for background purposes. Sample fluid 100 contains particles 101 and flows in the direction indicated by arrow 109. Sample fluid 100 is a liquid or a gas. Sample fluid 100 may be contained within a conduit (not shown) or may be a stream of fluid as shown in FIG. 1 and may be circular, square or otherwise in cross-sectional shape. Laser 102 produces a beam of light 103 that is shaped by beam shaping optics 104. The resulting beam 105 intersects sample fluid 100 and is incident upon particles 101. Scattered light 106 is caused by the scattering of beam 105 off of particles 101. Scattered light 106 is collected by collection optics 107 and imaged on detector 108. Beam 105 is absorbed in light dump 109 such that beam 105 does not reflect back into sample fluid 100. Detector 108 produces an output signal over path 110 that is indicative of particles 101. Processor 111 processes the output signal received over path 110 to produce an output representative of the size and/or number of particles 101 in sample fluid 100. There are various and multiple known alternatives for each of the basic elements shown in FIG. 1. For example, collection optics 107, shown in alignment with beam 105 in FIG. 1, could instead be positioned to collect light scattered on a different axis. Various different types of detectors 108 are known as are different types of processors 111. All of these various approaches and apparatuses are known to those skilled in the particle detection art and do not form part of the present invention.

Intersection region 112 is the area of intersection between sample fluid 100 and beam 105. Sample region 113 is the area within intersection region 112 from which scattered light 106 is imaged upon detector 108. There are multiple considerations including, but not limited to, measurement resolution and measurement sensitivity that determine the size of intersection region 112 and sample region 113. For example, a highly sensitive measurement (one capable of detecting relatively small particles) requires a tightly focussed light beam. There is a direct relationship between the size of the light beam and the sensitivity of the particle detection measurement since, for a given laser, a more focussed beam provides more power per unit area than a less focussed beam. A very narrow light beam, however, typically means that only a portion of the sample fluid passes through the intersection region (an in situ measurement). A disadvantage of in situ measurements is that not all particles are illuminated with light of the same intensity. Beam 105 has a gaussian intensity distribution thus a particle illuminated by an "edge" of beam 105 is illuminated with a lower intensity light than a particle illuminated in the center of beam 105. A further limitation is that scattered light 106 must be scattered by particles moving with a relatively uniform velocity. Processor 111 depends upon the assumption that all of scattered light 106 is scattered by particles 101 moving with relatively uniform velocity. Existing particle detection systems employ sample fluid streams characterized by laminar, developed flow (discussed in more detail with respect to FIG. 2) where a fluid velocity profile exists orthogonal to the flow direction. Thus even within the intersection region 112 there is, in existing systems, only a small portion of sample fluid 100 that is moving with relatively uniform velocity and is illuminated with a relatively uniform intensity of light. Sample region 113 is typically defined in existing particle detection systems such that only scattered light 106 from particles 101 moving with relatively uniform velocity and illuminated with relatively uniform light intensity is imaged on detector 108. This requirement further reduces the resolution of the detection system and increases the sample time. The size of sample region 113 is defined by sample fluid 100, beam 105 and collecting optics 107 to appropriately match detector 108, as known by those skilled in the particle detection art.

"Developed" and "inviscid" flow are described in further detail with respect to FIG. 2. FIG. 2 depicts a reservoir 200 filled with fluid 203 which flows from reservoir 200 through conduit 201. The nature of the flow of fluid 203 through conduit 201 at positions A–F is described. The dotted lines at positions A–F depict the velocity profile of fluid 203 through conduit 201 at the respective locations. At position A fluid 203 has just entered conduit 201 from reservoir 200 and the velocity profile at position A is uniform across the diameter of conduit 200. When all of the fluid is moving with relatively uniform velocity it is referred to herein as "inviscid" flow. At position B the velocity profile of fluid 203 has begun to develop due to the viscous drag between fluid 203 and the walls of conduit 201. Elements of fluid 203 traveling adjacent to or relatively close to the wall of conduit 201 move more slowly than elements of fluid 203 traveling along the center of conduit 201. Thus, the velocity profile at position B shows a relatively large area of uniform velocity along the center of conduit 201 but regions of decreasing velocity near the walls of conduit 201. The flow of fluid 203 continues to develop through positions C, D and E until at position F the fluid flow is fully "developed". Inviscid region 202 indicates the area of inviscid flow at each position along conduit 201. Thus at position A all or nearly all of fluid 203 moves at a uniform velocity thus the flow at position A is referred to as inviscid. At position D only the portion of the velocity profile within inviscid region 202 is inviscid flow. As the velocity profile develops from positions B to F, only the portion of the profile within inviscid flow region 202 is "usable" as a sample region for a particle detection system.
Particle Detection System of the Present Invention—FIGS. 3–13

Figure 3:
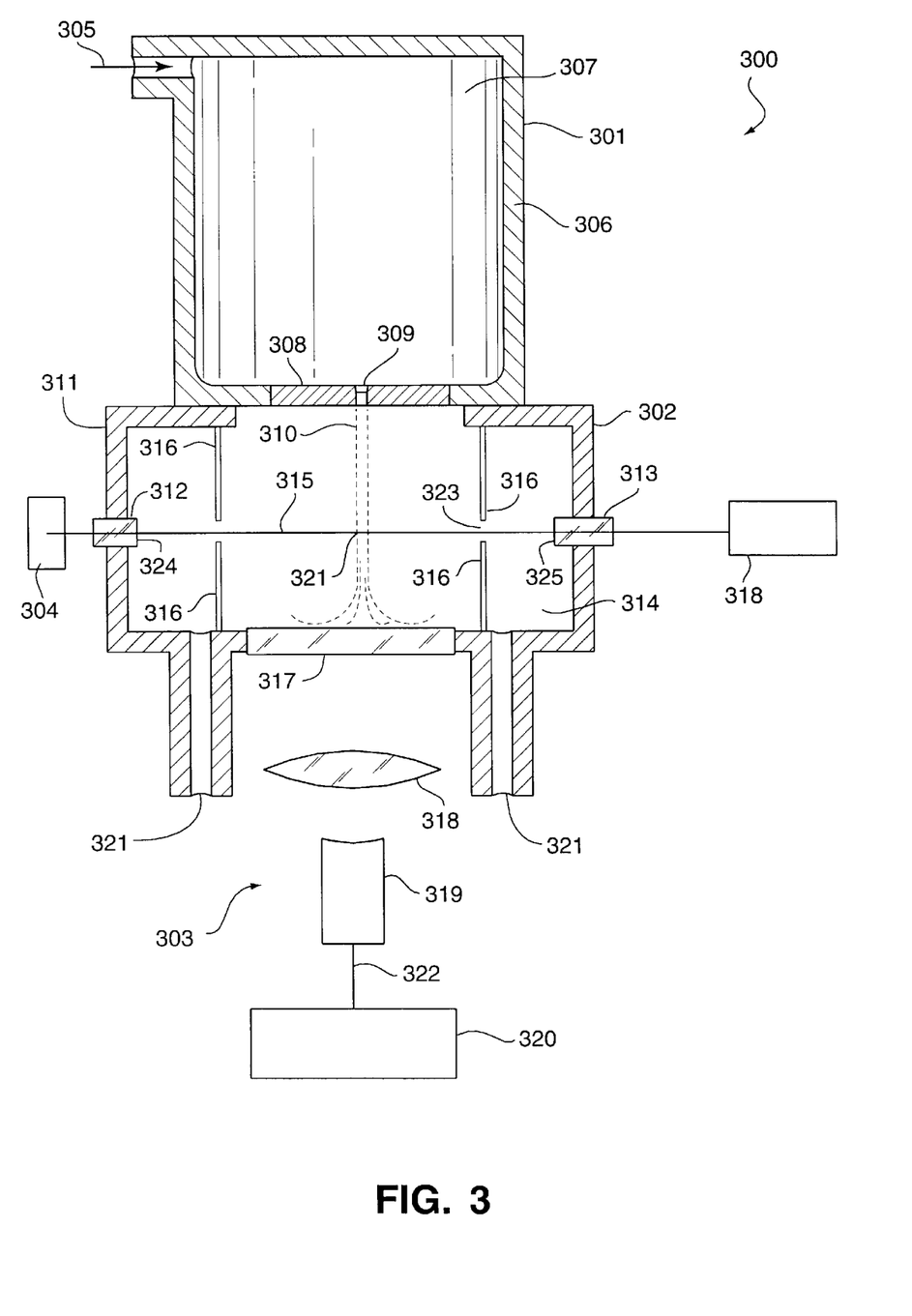
FIG. 3 is a sectional view of a particle detection system according to the present invention.

FIG. 3 depicts a particle detection system 300 according to the present invention. System 300 includes deceleration chamber 301, collection chamber 302, detection system 303 and illumination source 304. Deceleration chamber includes inlet 305 through which a sample fluid flows from a process line (not shown) through chamber wall 306 to an interior 307 of deceleration chamber 301. In the bottom of deceleration chamber 301 is inviscid flow nozzle 308 having aperture 309 formed therein. Sample fluid flows into inlet 305, through deceleration chamber 307 and into collection chamber 302 through inviscid flow nozzle 308 as inviscid fluid jet 310. The velocity of the sample fluid through deceleration chamber 301 is significantly less than the velocity of the fluid in inviscid flow jet 310. In an embodiment of the present invention the velocity through deceleration chamber 301 is approximately 1/40 that of the velocity of inviscid fluid jet 310. Inviscid fluid nozzle 308 and particularly aperture 309 are discussed in more detail with respect to FIGS. 4–5, 7–11.

Illumination source 304 produces beam 315 which passes through wall 311 of collection chamber 302 by way of illumination entrance window 312. Beam 315 intersects inviscid flow jet 310 at intersection region 321 and exits collection chamber 302 through illumination exit window 313. Light scattered by particles in the sample fluid at intersection region 321 passes through detection window 317 and is imaged by collector optics 318 on detector 319. Detector 319 produces signals over path 322 to processor 320. Processor 320 produces an output of particle size and/or number. Detection system 303 including collector optics 318, detector 319 and processor 320 are shown schematically in FIG. 3. Those skilled in the art of particle detection systems recognize that there are various known approaches satisfying the requirements of detection system 303.

Collection chamber 302 includes light stops 316 each of which includes an aperture 323. Light stops 316 block light scattered by the interfaces 324 and 325 between the interior of collection chamber 302 and illumination entrance window 312 and illumination exit window 313, respectively. Beam 315 is absorbed by light dump 318 so that beam 315 is not reflected back into collection chamber 302 or to detection system 303. The sample fluid exits collection chamber 302 through outlets 321 to a process line (not shown). Collection chamber 302 is full of sample fluid. Detection system 303 is operable to distinguish between a particle in inviscid flow jet 310 (moving at a relatively high velocity) and a particle outside of inviscid flow jet 310 (moving at a relatively low velocity), as is known to those skilled in the art. Those skilled in the art also recognize that additional outlets 321 may be used.

Figure 4:
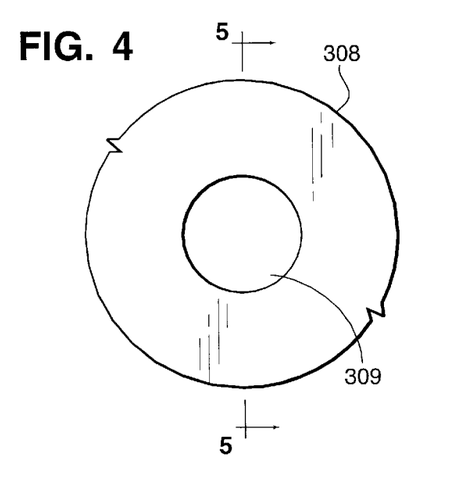
FIG. 4 depicts a top view of a circular inviscid flow nozzle according to the present invention.
Figure 5:
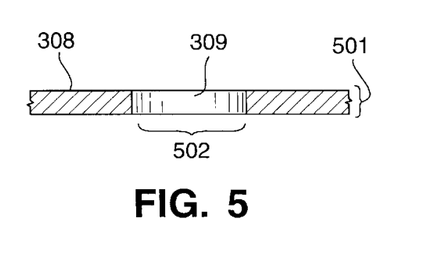
FIG. 5 depicts a sectional view of the circular inviscid flow nozzle of FIG. 4.

FIGS. 4 and 5 depict a top and sectional view, respectively, of a portion of inviscid flow nozzle 308 including aperture 309. Inviscid flow nozzle 308 has a thickness 501 and a nozzle diameter 502. Inviscid flow jet 310 is characterized as inviscid flow when the ratio of nozzle diameter 502 over nozzle thickness 501 is greater than or equal to one. This ensures that the distance traveled by the sample fluid through the nozzle is not long enough for the flow to develop a non-uniform velocity profile. Typical measurements for nozzle diameter 502 and nozzle thickness 501 are in the range of 0.001"–0.010".

Figure 6:
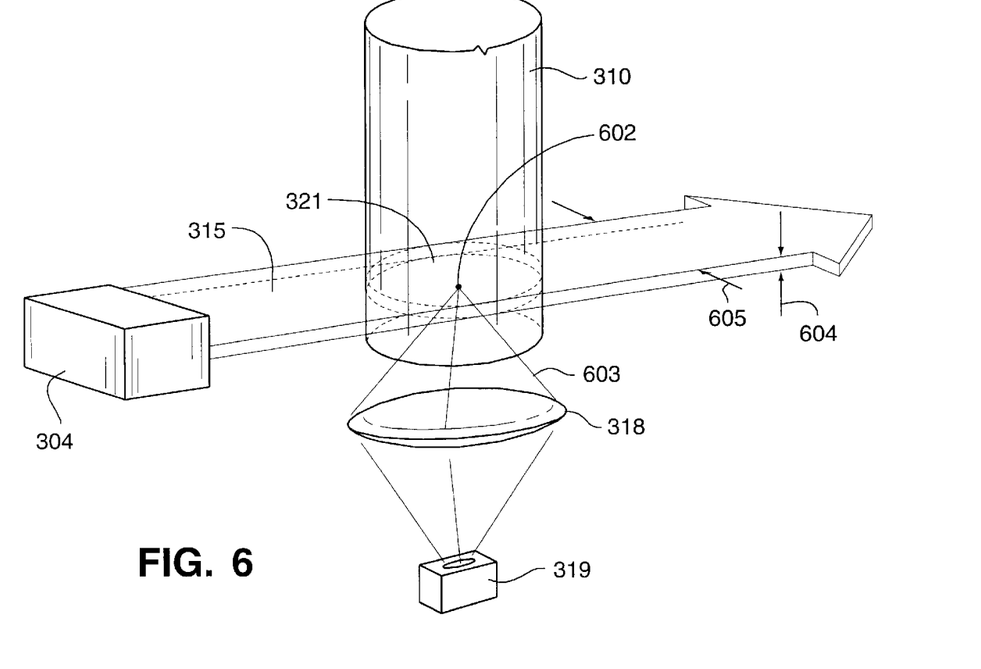
FIG. 6 depicts the intersection of a circular inviscid flow jet and a laser beam.

FIG. 6 schematically illustrates in greater detail the intersection region 321 between inviscid fluid jet 310 and beam 315. As noted with respect to FIG. 4, inviscid fluid jet 310 is characterized by the fact that all of the fluid within inviscid fluid jet 310 moves with a uniform velocity. Therefore, light scattered by any particle(s) passing through intersection region 321 is usable by detector 319 since all the particles are moving at the same or nearly the same velocity. Intersection region 321 is therefore also the sample region. Particle 602 is representative of the particles passing through intersection region 321. Light 603 from beam 315, scattered by particle 602, is collected by collector optics 318 and imaged upon detector 319 as described with respect to FIG. 3. Beam 315 is depicted in FIG. 6 as being matched to the diameter of inviscid fluid jet 310. Alternatively, resolution can be improved, at the expense of sensitivity, by increasing dimension 605 of beam 315 so that all of jet 310 is illuminated with relatively uniform intensity.

Figure 7:
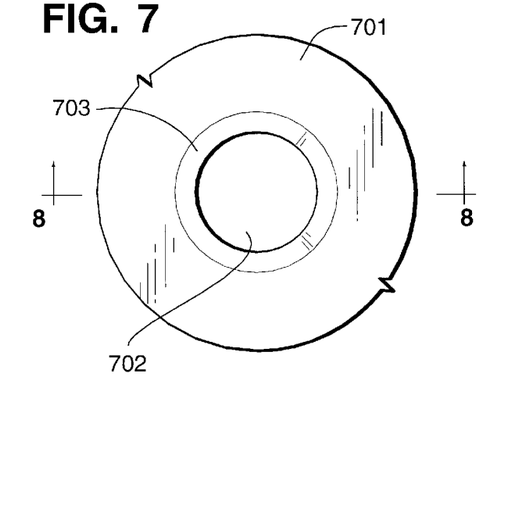
FIG. 7 depicts a top view of an alternative circular inviscid flow nozzle according to the present invention.
Figure 8:
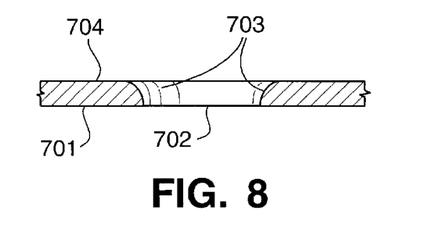
FIG. 8 depicts a sectional view of the circular inviscid flow nozzle of FIG. 7.

FIGS. 7 and 8 illustrate a portion of an alternative circular inviscid flow nozzle 701. Inviscid flow nozzle 701 has a circular aperture 702 as described with respect to inviscid flow nozzle 308. In addition, the interior surface 703 of aperture 702 is smoothly curved on the inlet side 704 of inviscid flow nozzle 701. The smoothly curved shape of interior surface 703 minimizes any turbulent flow eddies present in the inviscid fluid jet (not shown in FIG. 7) produced by inviscid flow nozzle 701. The smoothly curved shape of interior surface 703 also reduces the contraction of the fluid jet, i.e., vena contracts, as the jet exits the nozzle.

Figure 9:
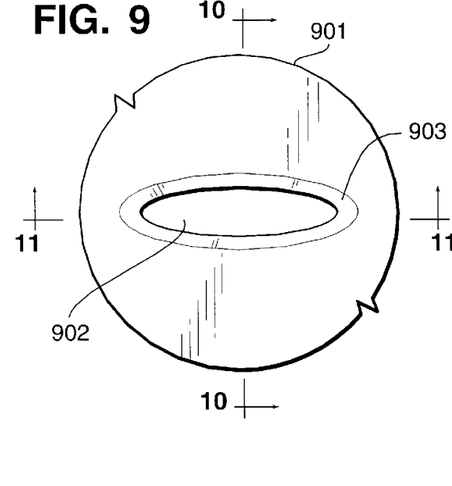
FIG. 9 depicts a top view of an oval inviscid flow nozzle according to the present invention.
Figure 10:
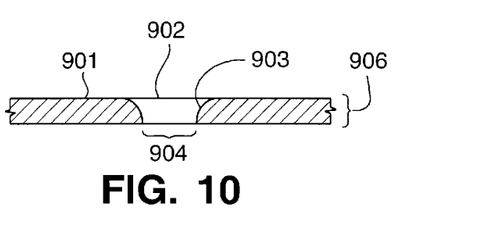
FIG. 10 depicts a sectional view of the oval inviscid flow nozzle of FIG. 9.
Figure 11:
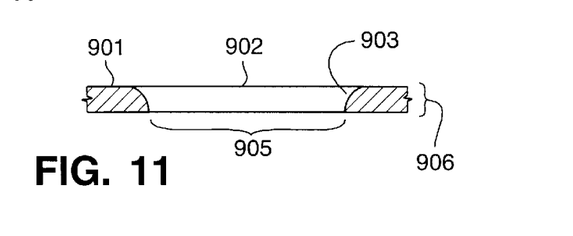
FIG. 11 depicts a further sectional view of the oval inviscid flow nozzle of FIG. 9.

FIGS. 9–11 illustrate a portion of a nozzle 901 employing an oval shaped nozzle aperture 902. Nozzle 901 also uses a smoothly curved interior surface 903 as described with respect to FIGS. 7–8 for reducing turbulent eddies in the produced inviscid flow jet. FIG. 10 depicts a sectional view through the short axis of oval shaped nozzle 901. FIG. 11 depicts a sectional view through the long axis of oval shaped nozzle 901. As with the circular nozzles of FIGS. 4–5 and 7–8, the diameter of the nozzle must be equal to or greater than the thickness of the nozzle in order to produce inviscid flow. Thus for nozzle 901, the ratio of diameter 904 to thickness 906 must be equal to or greater than 1. In an embodiment of the present invention, diameter 904 is equal to 0.008" and diameter 905 is equal to 0.064". The shape of aperture 902 need not be oval as shown in FIG. 9 or circular as shown in FIGS. 4–5, 7–8. Any shaped aperture is suitable that produces an inviscid flow jet.

Figure 12:
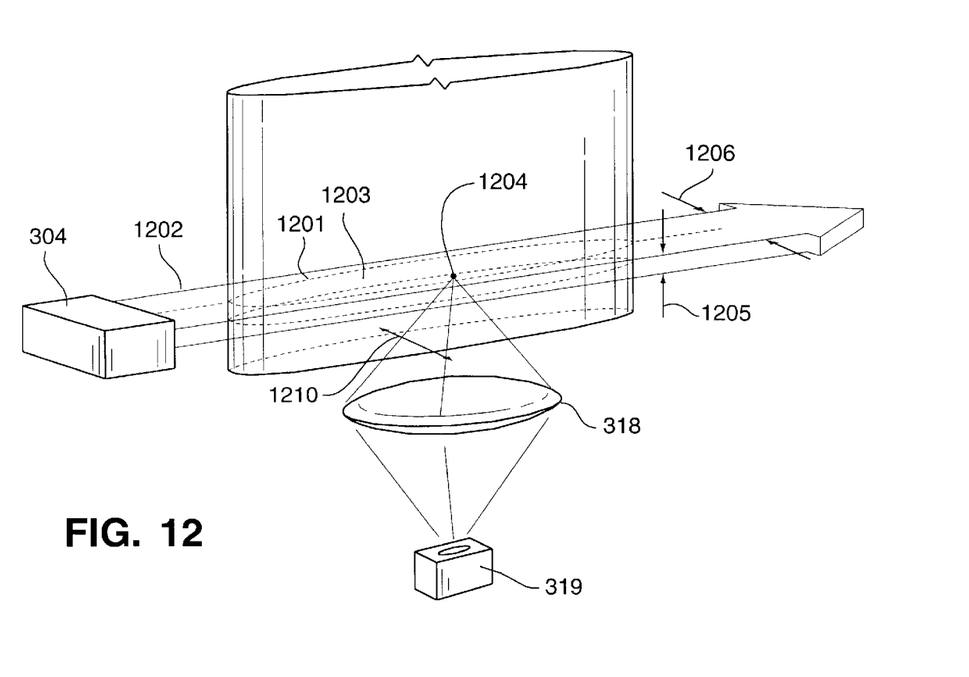
FIG. 12 depicts the intersection of an oval inviscid flow jet and a laser beam.

FIG. 12 is a schematic representation of the detail of intersection region 321 in an embodiment where nozzle 901 is used in place of nozzle 308 in FIG. 3. Light source 304 produces beam 1202 which is incident on inviscid flow jet 1201 substantially orthogonal to the short axis 1210 of inviscid flow jet 1201. Light scattered by particles (of which particle 1204 is representative) is collected by collector optics 318 and is imaged upon detector 319. Beam 1202 is more narrow than, for example, beam 315 of FIG. 6. The elongated shape of inviscid flow jet 1201 allows the incident light beam, beam 1202, to be narrowed down significantly and still fully and uniformly illuminate the entire inviscid flow jet. Thus, inviscid flow jet 1201 moves with uniform velocity, i.e., all particles moving at same velocity, and the entire jet is uniformly illuminated by beam 1202. Further, beam 1202.3 relatively narrowly focussed due to the high aspect ratio of jet 1201. This allows a particle measurement of high resolution and high sensitivity. In one embodiment of the present invention, beam 1202 is 0.014" wide (dimension 1206) and 0.0012" thick (dimension 1205) while jet 1201 is 0.008" on its short axis and 0.064" on its long axis. Collector optics 318 provides a magnifications of 6.25× thus detector 319 has an active area of 0.050"×0.400".

Figure 13:
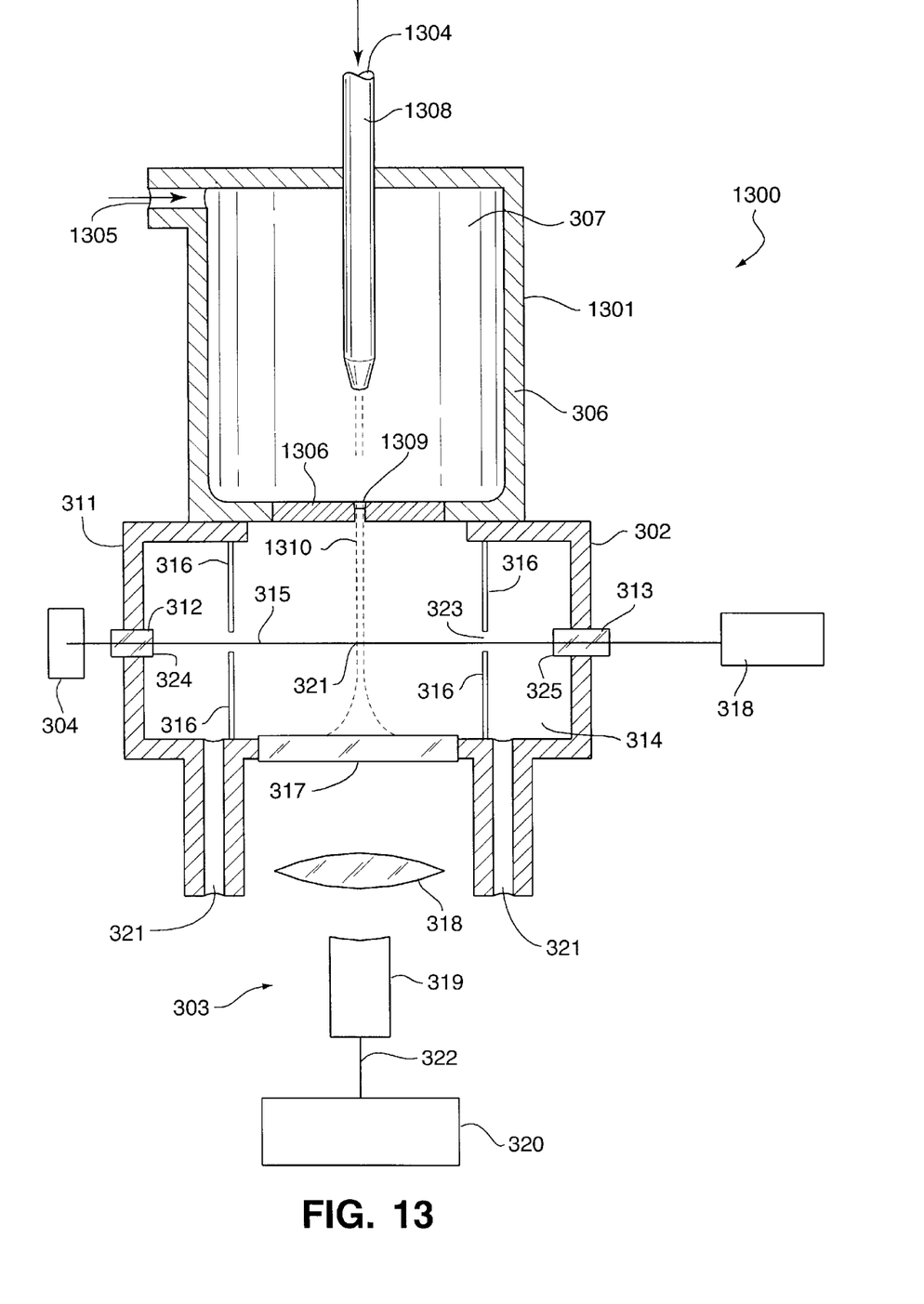
FIG. 13 is a sectional view of a further embodiment of a particle detection system according to the present invention.

FIG. 13 is a sectional view of a particle detection system 1300 according to the present invention. The embodiment of FIG. 13 is similar to the embodiment of FIG. 3 with the exception of additional elements, as discussed below, for producing an inviscid flow jet having a sheath flow. System 1300 includes deceleration chamber 1301, collection chamber 1302, detection system 1303 and illumination source 304. Deceleration chamber 1301 receives two separate flows, a sheath flow through inlet 1305 and a sample flow through inlet 1304, and merges the two flows using hydrodynamic focussing. The merged flows are presented to nozzle 1306. Nozzle 1306 is similar to the nozzle of FIGS. 9–11. Sample fluid 1307 is input to inlet 1304 of conduit 1308 from a process line (not shown). Sample fluid 1307 is the particle-containing fluid to be measured by system 1300. The sheath fluid flows into inlet 1305 from a second process line (not shown) through chamber wall 1306 to an interior 1307 of deceleration chamber 1301. Conduit 1308 is positioned in the center of deceleration chamber 1301 as is nozzle aperture 1309. The principle of hydrodynamic focussing allows for the sample fluid 1307 to be maintained in the center of the merged flow that is presented to nozzle 1306 and nozzle aperture 1309 as inviscid flow jet 1310. In the bottom of deceleration chamber 1301 is inviscid flow nozzle 1306 having aperture 1309 formed therein. Inviscid flow nozzle 1306 is formed substantially as shown in FIGS. 9–11. Sample fluid flows into inlet 1304 and is merged with sheath fluid from inlet 1305. The merged fluids flow through deceleration chamber 1301 and into collection chamber 1302 through inviscid flow nozzle 1306 as inviscid fluid jet 1310. The velocity of the sample fluid through deceleration chamber 1301 is significantly less than the velocity of the fluid in inviscid flow jet 1310.

Figure 14:
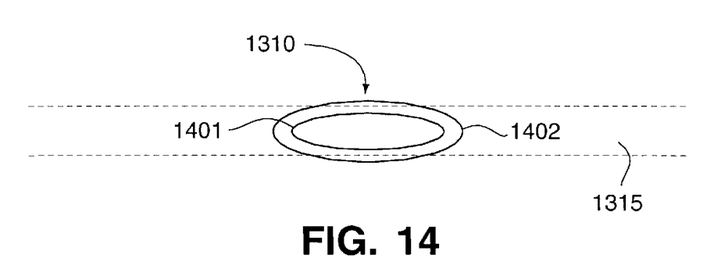
FIG. 14 is a cross-section through the inviscid flow jet produced by the apparatus of FIG. 13.

FIG. 14 illustrates a sectional view through inviscid flow jet 1310 along the axis of beam 1315 (intersection region 321). Inviscid flow jet 1310 is comprised of sample flow 1401 and sheath flow 1402. Beam 1315 is slightly wider than sample flow 1401 thereby illuminating all of the sample fluid. Use of sheath flow 1402 ensures that there is no velocity difference between the sample fluid and fluid adjacent to the sample fluid. This more stable flow allows for measurements with higher resolution. This also is advantageous where collection chamber 302 is actually a laser cavity as the sheath flow improves the stability of the laser cavity.

SUMMARY

The present invention provides for a volumetric particle detection measurement where the entire stream of sample fluid moves with uniform velocity. The inviscid jet may also be shaped to advantageously allow for relatively high sensitivity. This is accomplished by matching the shape of the inviscid jet to the shape of the incident light beam whereby a narrowly focussed light beam illuminates the entire jet. As a result, a jet of uniform velocity is illuminated with an intense and uniform light beam to produce particle detection measurements of high sensitivity and high resolution.

I claim:

1. A system for detecting submicron-sized particles in a sample fluid, comprising:

inviscid flow means for producing an inviscid fluid jet from said sample fluid;

illuminating means providing a beam of light directed toward said inviscid fluid jet, said light beam intersecting said inviscid fluid jet at an intersection region permitting volumetric sampling of said inviscid fluid jet in said intersection region wherein all of the particles are moving at substantially the same velocity through said intersection region scatter light from said beam of light for particle detection purposes; and detection means for receiving scattered light from said intersection region and providing an output indicative of said particles.

2. The particle detection system of claim 1 wherein said inviscid flow means includes:

fluid decelerating means having a sample fluid inlet through which said sample fluid is received;

a nozzle means to which said sample fluid flows from said sample fluid inlet at a decelerated velocity; and fluid collection means into which said inviscid fluid jet spurts from said nozzle means at a jet velocity wherein said decelerated velocity is less than said jet velocity.

3. The particle detection system of claim 2 wherein said fluid decelerating means includes:

a deceleration chamber having said sample fluid inlet and characterized by a deceleration chamber diameter wherein said deceleration chamber diameter is significantly larger than an inlet diameter of said sample fluid inlet.

4. The particle detection system of claim 2 wherein said fluid collection means includes:

an illumination entrance window aligned with said light beam to allow the passage of said light beam from said illumination means on an exterior of said fluid collection means to an interior of said fluid collection means.

5. The particle detection system of claim 4 wherein said fluid collection means includes:

an illumination exit window aligned with said light beam and said illumination entrance window to allow the passage of said light beam from said interior to said exterior.

6. The particle detection system of claim 5 wherein said fluid collection means includes:

light dump means aligned with said illumination exit window and said light beam for receiving said light beam whereby said light beam is not transmitted through or reflected by said light dump means.

7. The particle detection system of claim 2 wherein said fluid collection means includes:

a detection window through which said scattered light exits said fluid collection means towards said detection means.

8. The particle detection system of claim 7 wherein said detection means is positioned to receive said scattered light scattered substantially non-axially with respect to a flow axis of said fluid jet.

9. The particle detection system of claim 7 wherein said detection means is positioned to receive said scattered light scattered substantially axially with respect to a flow axis of said fluid jet.

10. The particle detection system of claim 2 wherein said nozzle means includes:

an inlet surface contiguous with an interior of said fluid decelerating means;

an outlet surface contiguous with an interior of said fluid collection means and separated by a nozzle thickness from said inlet surface; and a nozzle aperture between said inlet surface and said outlet surface through which said sample fluid flows and is emitted as said inviscid fluid jet into said fluid collection means.

11. The particle detection system of claim 10 wherein said nozzle aperture is characterized by a nozzle diameter, said nozzle diameter being at least as large as said nozzle thickness.

12. The particle detection system of claim 11 wherein said inlet surface has a rounded edge where said inlet surface is adjacent said nozzle aperture.

13. The particle detection system of claim 11 wherein said nozzle aperture is substantially circular and produces said inviscid flow jet having a substantially circular shape.

14. The particle detection system of claim 13 wherein said illuminating means includes:

beam shaping means for shaping said light beam whereby said light beam has known characteristics at said intersection region, said characteristics including a beam height and a beam width.

15. The particle detection system of claim 14 wherein said beam width is as large as a diameter of said inviscid fluid jet whereby all of said inviscid fluid jet is illuminated by said light beam at said intersection region.

16. The particle detection system of claim 14 wherein said detection means includes:

a detector for receiving said scattered light and producing a detector output responsive thereto;

processing means connected with said detector and, responsive to said detector output for providing a system output indicative of a particle characteristic.

17. The particle detection system of claim 16 wherein said beam height is substantially similar to a dimension of said detector.

18. The particle detection system of claim 11 wherein said nozzle aperture is substantially elliptical and produces said inviscid flow jet having a substantially elliptical shape characterized by a first jet diameter and a second jet diameter where said second jet diameter is significantly larger than said first jet diameter and said second jet diameter is oriented substantially parallel with respect to said beam of light to provide a high aspect ratio along said second jet diameter.

19. The particle detection system of claim 18 wherein said illuminating means includes:

beam shaping means for shaping said light beam whereby said light beam has known characteristics at said intersection region, said characteristics including a beam height and a beam width.

20. The particle detection system of claim 19 wherein said light beam is incident upon said inviscid fluid jet along an axis substantially orthogonal to said first jet diameter and said beam width is as large as said diameter first jet diameter whereby all of said inviscid fluid jet is illuminated by said light beam at said intersection region.

21. The particle detection system of claim 19 wherein said detection means includes:

a detector for receiving said scattered light and producing a detector output responsive thereto;

processing means connected with said detector and, responsive to said detector output for providing a system output indicative of a particle characteristic.

22. The particle detection system of claim 21 wherein said beam height is substantially similar to a dimension of said detector.

23. The particle detection system of claim 1 wherein said illuminating means includes:

beam shaping means for shaping said light beam whereby said light beam has known characteristics at said intersection region, said characteristics including a beam height and a beam width.

24. The particle detection system of claim 23 wherein said beam width is as large as a diameter of said inviscid fluid jet whereby all of said inviscid fluid jet is illuminated by said light beam at said intersection region.

25. The particle detection system of claim 1 wherein said detection means includes:

a detector for receiving said scattered light and producing a detector output responsive thereto;

processing means connected with said detector and, responsive to said detector output for providing a system output indicative of a particle characteristic.

26. The particle detection system of claim 25 wherein said particle characteristic is a particle size.

27. The particle detection system of claim 25 wherein said particle characteristic is a particle number.

28. A method for detecting submicron-sized particles in a sample fluid, comprising:

generating an inviscid fluid jet from said sample fluid;

directing a beam of light toward said inviscid fluid jet, said light beam intersecting said inviscid fluid jet at an intersection region for volumetric sampling of said inviscid fluid jet in said intersection region wherein all of the particles are moving at substantially the same velocity through said intersection region to scatter light from said beam of light for particle detection purposes; and detecting said scattered light and providing an output indicative of said particles.

29. The particle detection method of claim 28 wherein said generating step includes:

receiving said sample fluid through a sample fluid inlet decelerating said sample fluid;

presenting said sample fluid to a nozzle means at a decelerated velocity; and collecting said inviscid fluid jet fluid from said nozzle means wherein said inviscid fluid jet spurts from said nozzle means at a jet velocity wherein said decelerated velocity is less than said jet velocity.

30. The particle detection method of claim 29 wherein said decelerating step includes:

decelerating said sample fluid received from said sample fluid inlet in a deceleration chamber characterized by a deceleration chamber diameter wherein said deceleration chamber diameter is significantly larger than an inlet diameter of said sample fluid inlet.

31. The particle detection method of claim 29 wherein said presenting step includes:

presenting said sample fluid to an inlet surface of said nozzle means; and passing said sample fluid through a nozzle aperture of said nozzle means to an outlet surface of said nozzle means wherein said inlet surface and said outlet surface are separated by a nozzle thickness.

32. The particle detection method of claim 29 wherein said presenting step includes:

presenting said sample fluid to said nozzle means wherein said nozzle aperture is characterized by a nozzle diameter, said nozzle diameter being at least as large as said nozzle thickness.

33. The particle detection system of claim 32 wherein said inlet surface has a rounded edge where said inlet surface is adjacent said nozzle aperture.

34. The particle detection method of claim 32 wherein said presenting step includes:

presenting said sample fluid to said nozzle means wherein said nozzle aperture is substantially elliptical and produces said inviscid flow jet having a substantially elliptical shape characterized by a first jet diameter and a second jet diameter where said second jet diameter is significantly larger than said first jet diameter.

35. The particle detection method of claim 34 wherein said directing step includes:

shaping said light beam whereby said light beam has known characteristics at said intersection region, said characteristics including a beam height and a beam width.

36. The particle detection method of claim 35 wherein said directing step includes:

focussing said light beam upon said inviscid fluid jet along an axis substantially orthogonal to said first jet diameter and said beam width is as large as said diameter first jet diameter whereby all of said inviscid fluid jet is illuminated by said light beam at said intersection region.

37. The particle detection method of claim 36 wherein said detecting step includes:

receiving said scattered light and producing a detector output responsive thereto;

processing, responsive to said detector output, for providing a system output indicative of a particle characteristic.

* * * * *